United States Patent [19]

Buckland et al.

[11] Patent Number: 4,994,576

[45] Date of Patent: Feb. 19, 1991

[54] METHOD FOR REDUCING AROMATIC NITRO GROUPS

[75] Inventors: Paul R. Buckland, St. Albans; Robert N. Gourley, Aylesbury, both of Great Britain

[73] Assignee: Eastman Kodak Company, Rochester, N.Y.

[21] Appl. No.: 358,048

[22] Filed: May 30, 1989

[30] Foreign Application Priority Data

Jun. 14, 1988 [GB] United Kingdom ............... 8814003

[51] Int. Cl.$^5$ ............................................. C07D 231/00
[52] U.S. Cl. ..................................... 548/367; 564/417
[58] Field of Search ......................... 564/417; 548/367

[56] References Cited

U.S. PATENT DOCUMENTS

| | | | |
|---|---|---|---|
| 2,187,820 | 8/1938 | Lecher et al. ...................... | 564/417 |
| 3,798,271 | 3/1974 | Podschus et al. ................... | 564/417 |
| 4,066,660 | 1/1978 | Brown ................................ | 548/484 |
| 4,820,452 | 4/1989 | Lund et al. ......................... | 260/510 |

FOREIGN PATENT DOCUMENTS 221021 5/1985 European Pat. Off. .
59-216855 12/1984 Japan .................................. 564/417

OTHER PUBLICATIONS

Owsley et al., *Synthesis* (1977) pp. 118–119.
Béchamp, *Annales de Chemie* (1854) pp. 186–196.
*Annal. d. Chemie u. Pharm.*, vol. XCII, Issue 3, pp. 401–403.
Morrison and Boyd, *Organic Chemistry*, Fifth Edition, pp. 939–943 (1987).

*Primary Examiner*—Glennon H. Hollrah
*Assistant Examiner*—Scott C. Rand
*Attorney, Agent, or Firm*—Robert A. Linn

[57] ABSTRACT

This invention relates to a method for reducing a nitro group substituent on an aromatic compound to an amino group and is characterized by treatment of the compound in the presence of iron or zinc and a halogen-containing aliphatic carboxylic acid.

6 Claims, No Drawings

METHOD FOR REDUCING AROMATIC NITRO GROUPS

The invention relates to a method for reducing compounds containing aromatic nitro groups to the corresponding amines.

The iron/acid reduction of aromatic nitro compounds to amines has been used extensively since its discovery by Bechamp over 100 years ago (see A. Bechamp, Ann. Chim. (Paris) 1854, 42, 180 and A. Bechamp, Justus Liebigs Ann. Chem. 1854, 92, 401). However, the first published systematic study of the reduction of nitro compounds by iron/acetic acid did not appear until 1977 (see D.C. Owsley and J. J. Bloomfield, Synthesis 1977, 2 118). This later reference indicates that use of glacial acetic acid leads to the formation of anilides as the major or exclusive product, whereas use of acetic acid in ethanol leads predominately rather than exclusively to the aniline.

Similar methods involving mixtures of acetic acid and a mineral acid are known. For example, European Patent No. 221,021 describes used of a mixture of acetic acid and sulphuric acid which is said to be cheaper than acetic acid alone. U.S. Pat. No. 4,066,660 uses a mixture of acetic acid and ethanol, while U.S. Pat. No. 3,798,271 uses formic or acetic acid in the presence of water and an organic solvent such as xylene, benzene or toluene.

The present invention relates to an improved method for reducing aromatic nitro groups to form amines in good yields with little or no unwanted anilides.

According to the present invention there is provided a method of reducing an aromatic nitro ($-NO_2$) group to the corresponding amine ($-NH_2$) group by treatment with iron or zinc metal and a halogen-containing aliphatic carboxylic acid.

The halogen-containing acids may, for example, be trichloro-, dichloro- or trifluoroacetic acid, or mixtures thereof. Mixtures of such halogenated acids with non-halogenated acids, e.g. acetic acid, may also be used. The reaction mixture may also contain water and/or organic solvents.

The reaction can take place at ambient or elevated temperatures, for example, in the range of from 20° to 100° C., preferably at 65°-85° C., and especially at 70°-75° C.

The invention is illustrated by the following examples:

EXAMPLE 1

1-(2,3,4,5,6-Pentachlorophenyl)-3-(2'-chloro-5'-amino-anilino)-2-pyrazolin-5-one Iron powder (3.5 g) was added in portions over five minutes to a slurry of 1-(2,3,4,5,6-pentachlorophenyl)-3-(2'-chloro-5'-nitroanilino)-2-pyrazoline-5-one (5 g) in trifluoroacetic acid (50 ml) at 70° C. The yellow color of the nitropyrazolone rapidly disappeared, and after stirring at 70°-75° C. for ten minutes the hot solution was separated from any unreacted iron and added to stirred ice-water (400 ml). The resultant off-white precipitate of the aminopyrazolone was filtered off, washed with water and dried. The yield was 4.6 g (98%); single spot by thin layer chromatography.

EXAMPLE 2

The title compound from Example 1 was prepared by the method described therein, except that DICHLOROACETIC ACID was used instead of TRIFLUOROACETIC ACID. The yield was 91%, with similar purity to the Example 1 product.

The invention has been described in detail with particular reference to preferred embodiments thereof, but it will be understood that variations and modifications can be effected within the spirit and scope of the invention.

We claim:

1. A method for reducing an aromatic nitro ($-NO_2$) group to the corresponding amine ($-NH_2$) group which comprises treating a benzene compound having a nitro group with iron or zinc metal and a halogen-containing aliphatic carboxylic acid, said acid being selected from trichloro-, dichloro-, or trifluoro-acetic acid; said method being further characterized by making little or no anilide.

2. Method of claim 1 wherein said metal is iron.

3. Method of claim 2 wherein 1-(2,3,4,5,6-pentachlorophenyl)-3-(2'-chloro-5'-nitroanilino)-2-pyrazoline-5-one is reduced to 1-1-(2,3,4,5,6-pentachlorophenyl-3-(2'-chloro-5'-amino-anilino)-2-pyrazolin-5-one with iron and an acid selected from trifluoroacetic acid and dichloroacetic acid.

4. The method of claim 1 wherein the reaction mixture also contains another acid, water and/or organic solvent.

5. The method of claim 1 wherein the reaction takes place at a temperature of from 65° to 85° C.

6. The method of claim 5 wherein the reaction takes place at a temperature of from 70° to 75° C.

* * * * *